(12) United States Patent
Gunther

(10) Patent No.: US 11,266,477 B2
(45) Date of Patent: Mar. 8, 2022

(54) MODULAR STORAGE SYSTEM FOR MEDICAL NEEDLES

(71) Applicant: NEEDLERAY SYSTEMS LTD, Windsor (GB)

(72) Inventor: Clive Peter Gunther, Haslemere (GB)

(73) Assignee: NEEDLEBAY SYSTEMS LTD, Windsor (GB)

( * ) Notice: Subject to any disclaimer, the term of this patent is extended or adjusted under 35 U.S.C. 154(b) by 200 days.

(21) Appl. No.: 16/976,068

(22) PCT Filed: Sep. 19, 2016

(86) PCT No.: PCT/EP2016/072210
§ 371 (c)(1),
(2) Date: Aug. 26, 2020

(87) PCT Pub. No.: WO2018/050261
PCT Pub. Date: Mar. 22, 2018

(65) Prior Publication Data
US 2021/0137629 A1   May 13, 2021

(51) Int. Cl.
*A61B 50/30* (2016.01)
*A61B 50/00* (2016.01)

(52) U.S. Cl.
CPC .. *A61B 50/3001* (2016.02); *A61B 2050/0051* (2016.02); *A61B 2050/3008* (2016.02); *A61B 2050/3009* (2016.02)

(58) Field of Classification Search
CPC ........ A61B 50/3001; A61B 2050/0051; A61B 2050/3008; A61B 2050/3009; A61B 50/30; A61B 50/20
(Continued)

(56) References Cited

U.S. PATENT DOCUMENTS 5,356,385 A * 10/1994 Latini ................. A61M 5/3213
206/366
5,855,285 A    1/1999 Laird et al.
(Continued)

FOREIGN PATENT DOCUMENTS

| EP | 0914805 A1 | 5/1999 |
| WO | 02100465 A1 | 12/2002 |

(Continued)

OTHER PUBLICATIONS

International Search Report and Written Opinion dated May 18, 2017, for corresponding PCT Application No. PCT/EP2016/072210.
(Continued)

*Primary Examiner* — Rafael A Ortiz
(74) *Attorney, Agent, or Firm* — Kinney & Lange, P.A.

(57) ABSTRACT

A modular storage system is described for storing and/or shielding a hypodermic needle which includes a modular needle container element for storing and/or shielding a hypodermic needles. The system includes a compartment for storing the needle, defined by first and second walls configured to be end walls, and a front wall and a rear wall extending between the first and second walls; each of the first and second walls has an outer surface directed away from the compartment, and each of the first and second walls include either a male connector on the outer surface of the wall or a female connector extending through the wall. The male connector includes a clip arm and the female connector includes a slot, such that the male connector is configured for engagement in a snap-fit manner to the female connector in the first or second wall of a second container element.

11 Claims, 7 Drawing Sheets

(58) Field of Classification Search
USPC .............. 206/363–366, 223, 504, 571, 438
See application file for complete search history.

(56) References Cited

U.S. PATENT DOCUMENTS

| | | | | |
|---|---|---|---|---|
| 2002/0014430 A1* | 2/2002 | Groth | ..................... | B65D 85/24 |
| | | | | 206/438 |
| 2006/0169611 A1* | 8/2006 | Prindle | ................. | A61M 5/002 |
| | | | | 206/364 |
| 2010/0051491 A1* | 3/2010 | Lampropoulos | ....... | A61B 50/20 |
| | | | | 206/366 |
| 2016/0166349 A1* | 6/2016 | Guichet | ................. | A61B 50/10 |
| | | | | 206/363 |

FOREIGN PATENT DOCUMENTS

| | | | | | |
|---|---|---|---|---|---|
| WO | | 2007132237 A1 | 11/2007 | | |
| WO | WO-2007132237 A1 | * | 11/2007 | ......... | A61B 50/3001 |
| WO | | 2016138047 A1 | 9/2016 | | |

OTHER PUBLICATIONS

International Preliminary Report on Patentability dated Mar. 19, 2019, for corresponding PCT Application No. PCT/EP2016/072210.

* cited by examiner

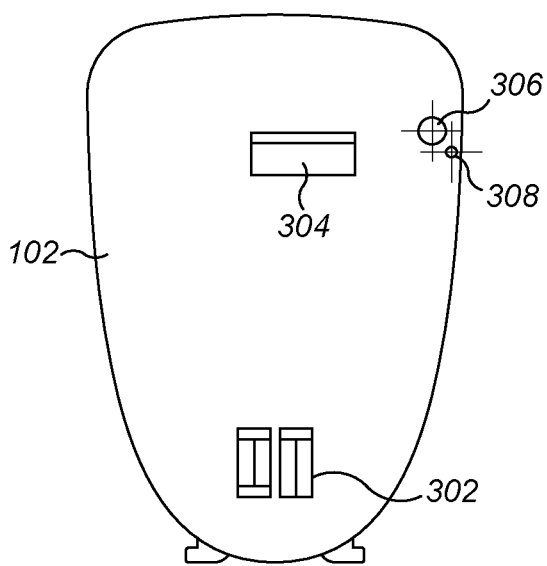
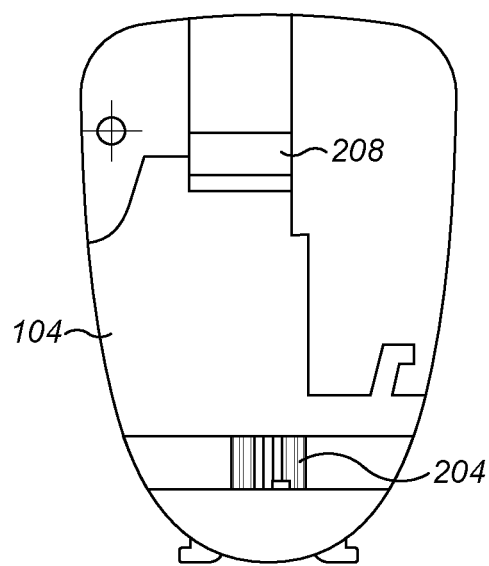
FIG. 3a    FIG. 3b
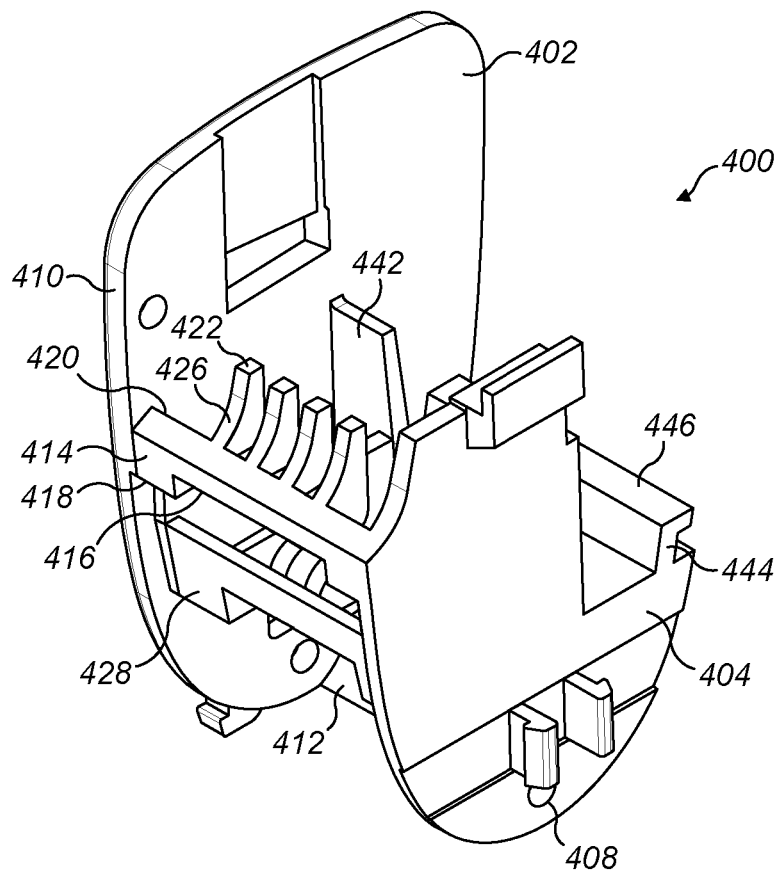
FIG. 4a

MODULAR STORAGE SYSTEM FOR MEDICAL NEEDLES

CROSS-REFERENCE TO RELATED APPLICATION(S)

This application is a Section 371 National Stage Application of International Application No. PCT/EP2016/072210, filed on Sep. 19, 2016, entitled "MODULAR STORAGE SYSTEM FOR MEDICAL NEEDLES" by Clive Peter Gunther, the whole disclosure of which is incorporated herein by reference.

TECHNICAL FIELD

This disclosure relates to a modular storage system for storing and/or shielding a needle. Some embodiments of the disclosure provide a container for assisting in the management of diabetes. Alternative embodiments can be used to safely dispose of sharps or spent needles. Individual containers, or bays, designed to hold pills or needles can be connected in an arrangement that reflects the individual medical needs of each user. For example, treatment plans for diabetes patients vary a lot, and therefore a single medication management system would not be appropriate for every user. Some embodiments of the disclosure can allow a user to store all medication for each day in a single device, according to their particular needs, and it is easily seen if a dose has been missed that day.

BACKGROUND

There are many situations and patients in the healthcare industry that require daily use of needle and other sharps. Professionals are trained in the safe storage, use and disposal of these sharps in order to reduce needle stick injuries which they may experience. However there are many lay people, not medically trained, who handle needles on a daily basis. Those with diabetes fall into this group, as do patients suffering from any disease that requires regular, self-administered injections. These people are vulnerable to needle stick injuries, and it is desirable to try and reduce the risk of such injuries.

Diabetes is a common, life-long metabolic disease. It is estimated that there are 3.2 million patients in the UK alone. A person with diabetes cannot regulate the levels of glucose in their blood. This is controlled by a hormone called insulin, produced in the pancreas that allows the glucose to be used as fuel by the body. There are two main types of diabetes. In the first, Type 1 diabetes, the pancreas does not produce any insulin. In the second, Type 2 diabetes, not enough insulin is produced to regulate the levels of glucose in the blood, or the insulin produced is not effective as the cells of the body do not respond to it properly.

There is no medication to cure diabetes. It is a condition that must be managed by the patient every day. The most common medication used by a diabetes patient is insulin, to replace the naturally made insulin that the pancreas does not produce. Normal digestion prevents insulin being effective after ingestion, so it must be injected. In addition to insulin a patient may be advised by their doctor to take supplementary medication to control related issues such as blood pressure, blood sugar and blood fats. Alternative medications can be prescribed, particularly for those with Type 2 diabetes, to improve sensitivity of the body tissues to insulin, or promote the excretion of more insulin.

Overall, a single diabetes treatment plan can be very complicated, individual to the needs of each patient, and requiring of constant monitoring. The regularity of administration and dependency on diet and physical exercise can make a treatment plan difficult to follow. It is vital that each patient regulates their own glucose levels, not just in order to ensure that they have sufficient energy. There are serious dangers when glucose levels in the blood are too high or too low; hypoglycemia can result when the levels of glucose in the blood are critically low, and can lead to brain damage or death in its most serious forms; hyperglycemia occurs when there is an excessive amount of glucose in the blood, and if untreated over a long period of time, can result in heart disease or heart failure.

Insulin injections are often seen as the most difficult aspect of a diabetes treatment plan to follow. The injection process is unpleasant, especially for children. Injection pens and pen needles are expensive, and the transport and storage of the pen needles is rarely convenient. However it is important to not only follow a treatment plan for the reasons set out above, but to administer the medication in a manner that is safe and hygienic. The risk of needle sticks when removing used needles from a pen is high. This is a particular risk for a carer, assisting in the delivery of the insulin, who should at no point come into contact with the end of a needle used on another person. Additionally, there is a risk that those with diabetes may attempt to reuse needles to minimize costs or limit the number of pen needles they are required to carry with them each day. This can increase the risk of those with diabetes developing lipohypertrophy, and should be avoided.

There are devices on the market to aid in the delivery and monitoring of medication, including medication for diabetes. Complicated electrical timers, timers inbuilt to injection pens and smart phone apps can all be used to provide reminders to take medication.

Containers for the needles to be used with injection pens allow needles to be stored individually, in sterile environments, and provide the secondary benefit of receiving the needle again after use for disposal, so that the user does not need to come into direct contact with it after use. These containers are disposed of with the needles so a new one must be bought for each needle.

It would be desirable to provide a diabetes medication management system that is simple, reusable, adaptable for different treatment plans, safe and hygienic.

SUMMARY

The present disclosure provides a modular storage system for storing and/or shielding a hypodermic needle including: a modular needle container element for storing and/or shielding a hypodermic needle, said needle container element including a rigid first wall and a rigid second wall opposing the first wall, the needle container element further including a compartment for storing said needle, defined by the first and second walls configured to be end walls, and a front wall and a rear wall extending between the first and second walls; each of the first and second walls has an outer surface directed away from the compartment, and each of the first and second walls include either a male connector on the outer surface of the wall or a female connector extending through the wall; wherein the male connector includes a clip arm and the female connector includes a slot, such that the male connector is configured for engagement in a snap-fit manner to the female connector in the first or second wall of a second container element.

It can be advantageous to provide a medication management system for a healthcare professional or a lay person, in particular a lay person with diabetes, which can be built by attaching together a combination of modular containers to create the required storage for the patients' individual treatment plan. Advantageously they can be arranged in the order in which they are to be taken throughout the day, limiting the possibility of mixing up doses or timings. This can also act as a clear visual reminder to ensure that by the end of the day all necessary doses have been taken. A single container carrying only the medication required for a single day minimizes what those with diabetes have to carry on their person on the average day. Overall, it provides a very convenient and efficient way of storing and transporting medication for diabetes or diseases with similar treatment plans.

The snap-fit assembly is used in order to be the simplest configuration for manufacture and construction. The mechanism is simple yet very secure and cannot easily come apart by accident. The rigid structure that will not deform under the sorts of stresses a container might experience when being kept in a pocket or a bag will protect the medication held within each container and provide a container that is convenient for holding during use.

In certain embodiments, the system further includes a modular medication container element for storing and/or dispensing medication; said medication container element including a rigid first wall and a rigid second wall opposing the first wall, the medication container element further including a compartment for storing said medication, defined by the first and second walls configured to be end walls, and a base wall extending between the first and second walls; each of the first and second walls has an outer surface directed away from the compartment, and each of the first and second walls include either a male connector on the outer surface of the wall or a female connector extending through the wall.

As well as combinations of injectable medications requiring needles to be stored, it is common for those with diabetes to combine their insulin regimes with other forms of medication provided in pill, tablet or capsule forms. It may be advantageous to be able to incorporate a container for these forms of medication into a system storing the needles used as well such that the full treatment plan can be stored and transported together.

These medication containers also provide a clear visual reminder to ensure that all required doses of both types of medication are taken.

In certain embodiments, the storage system includes further modular needle or medication container elements that are connectable in a linear arrangement with the said modular container element, such that the male connector of one engages with the female connector of the other. These walls may be referred to as end- or side-walls interchangeably. This is a stable, easily manufactured arrangement of containers. The timeline of medication to be taken can clearly be seen from one end of the linear arrangement to another.

In certain embodiments, the first or second wall includes a hook on the outer surface of the wall and the first or second wall includes an opening extending through the wall to receive the hook, such that the hook is configured for engagement with the opening in the first or second wall of a second container element.

This addition provides extra stability in the connection of the containers. While the clip arm may be removed from the slots in a neighboring container with enough force, the hook will withstand a much larger force. The combination of connecting means ensures the side walls of neighboring containers are held flush against each other.

In certain embodiments, the hook is positioned on the outer face of the first or second wall that includes the clip arm and the opening is positioned through the first or second wall that includes a slot.

The hook may be located at a different part of the first side wall, such as the top while the clip arm is closer to the base, or visa versa. Providing both of the male connecting means on the same wall, and therefore both female connecting means on another wall make manufacture of the walls easier.

In certain embodiments, the storage system includes an end plate element, said end plate element comprises a rigid wall, couplable to the first or second wall of said container element.

This end plate may be used on a single container if a patient only requires a single dose of medication to be stored. One may be positioned at each end of the modular system, or only one may be positioned at a single end.

In certain embodiments, the end plate element has two opposing surfaces, a first smooth surface and a second surface including either a male connector on the second surface or a female connector extending through the end plate element.

In certain embodiments, the male connector includes a clip arm and the female connector includes a slot, such that the male connector is configured for engagement in a snap-fit manner to the female connector in the first or second wall of a container element.

An end plate can create a closed end to the linear modular system such that the compartments within the containers, holding the medication, do not get contaminated. They also create flat exposed ends that are not at risk of getting caught on other objects.

The system, once connected could function without the end plates. In the preferred embodiment of the present disclosure however an end plate is included. This is because if a container at the end of the linear arrangement had an exposed surface with male connectors, these connectors would be projecting from the system and could be damaged or caught on other objects. If the exposed surface had female connectors, openings in the side wall, then germs and dust, etc., could enter the container and the contents may become dirty. This is not a severe concern if the container is holding needle casings, wherein the needle is held in a sterile environment within the casing. However if the container is housing loose oral medication such as pills or tablets, the inner compartment of the container would preferably be kept as clean as possible. Additionally the end plate may provide the hinge point for the access door of the end container, so it is used in the embodiment described below.

In certain embodiments, each container element may be a needle container element for receiving a casing for a hypodermic needle.

A large proportion of those with diabetes require regular insulin injections. This is usually performed using a reusable injection pen and removable, disposable needles. These needles must be stored in a sterile environment before use, they are usually provided in a sterile, sealed needle casing, and it is common nowadays and can be advantageous to have a mechanism provided with the needle for its safe removal from the pen after use to aid with disposal and minimize needle sticks. A mechanism that allows for simple storage and transport of multiple needles, and provides a mechanism to store used needles in a way they cannot be accessed for a second time reduces the practice of re-using needles and limits the risks of complications such a lipohypertrophy.

Not only may it be advantageous to provide a container designed to securely retain a needle holder before use, but also during use of the needle and after use of the needle, before disposal. A container that can secure a needle holder while the pen is attaching to the needle may be advantageous. As is a container that can secure a needle holder while the needle is being removed from the pen and returned to the holder, and can dispose of the holder and used needle in a way that reduces the risk of needle sticks. The mechanism may be referred to as 'touch-free', as at no point does the user need to come in direct contact with the needle in order to use it.

In certain embodiments, each container element may alternatively be a pill container element for receiving medication for oral administration.

Many of those with diabetes manage their disease or side effects of it with pills or tablets. It may be required for a patient to take these throughout the day, with or instead of insulin injections. Pills and tablets are usually much smaller than needle holders. They may get damaged being stored and transported in a large container, so it may be advantageous to provide a container designed specifically for them.

A treatment plan for diabetes is often a combination of insulin that must be injected and tablets or pills that must be taken orally. It would greatly benefit the patient to be able to store both forms of medication at once and visualize which have been taken in the correct order throughout the day. The primary and secondary containers can be different sizes or shapes to store different sorts of medication, such as pills or needles. They can be different colors to differentiate between different types of pills or needles, such as to indicate different types of medication, for example slow or fast acting insulin that are administered using the same types of needle but are required at different points during the day.

In certain embodiments, the needle container element includes an needle support structure within the compartment, and a pivotable clamping element; the clamping element including a first end portion and a second end portion, wherein the first end portion is pivotably connected to a wall of the needle container element and the second end of the clamping element comprises a substantially U-shaped clamp, such that the clamping element is pivotable from a first position in which a needle casing within the needle container element is not in contact with the U-shaped clamp, to a second position in which the U-shaped clamp is engaged with the needle casing.

Needle casings are usually sold alone or in combination with other identical casings. They can be used alone, with a user holding the casing between their fingers when screwing the injection pen into the connecting end of the needle assembly. However the risks of needle sticks, or accidents such as dropping the casing are high if using the casing in this manner as they are small and difficult to handle. It is common that a user has impaired dexterity or diabetic neuropathy, and therefore requires a device that is ergonomic. It may therefore be advantageous to provide a means of allowing the casing to be retained in a larger container that will hold it securely such that a user can hold the larger container with more ease and reduce accidents or needle sticks. The most common form of retention is clamping. A clamping mechanism is easy to operate and simple to manufacture.

It can sometimes be advantageous to provide a container into which a needle casing can be clamped to prevent it moving within the container and getting damaged. A container is larger than just the needle casing and therefore easier to hold, which may reduce accidents during use. As discussed above, a clamping mechanism provides a secure attachment means for the casing within the container. The larger the surface area connecting the clamps to the casings, the better grip the clamps will have on the casing. As the casing is being clamped around a cylindrical lower portion, U-shaped champs that have a concave inner surface to engage with the curved outer surface of the casings can be advantageous. A pivotable clamping element is preferable to a completely removable clamping element as it eliminates the risk of losing the clamping element.

In certain embodiments, it is desirable to provide a way for a user or an injector pen to access the casing within it, but it to also be sealed, hence a pivotable access door. This is pivotable in the embodiment described in detail below for the same reasons that the clamping element is pivotable, but it need not be. The same access door may be used on pill containers and needle containers. On a pill container the access door provides the only opening in the walls of the compartment. It is used to insert and access pills or tablets from within the compartment. For a needle container the access door is opened to insert the needle casing into the compartment, but also to access the needle itself. An injector pen can be inserted through the access door into the top opening of a commercially available needle casing. It can screw onto the needle, the needle can be used, and the needle can be returned to the casing for storage before disposal. The access door can enclose the needle casing even after the needle is used, providing a convenient and compact storage device that can retain the used needles until it is convenient to dispose of them.

As no complex clamping mechanism is required for the pill container it can be advantageous to minimize the points at which contaminates could enter the container, hence the outer edge of the pill container is closed by a base wall that extends from one end of the access door to the other end of the access door.

In certain embodiments, the male connector includes two clip arms and the female connector includes a slot, such that the arms are configured to engage in a snap-fit manner with the slot of a second container.

The attachment means is preferably simple to use and to manufacture. Compressible clips arms provide such a simple means. The two arms extend from one side of a modular container and are configured to align with the receiving slot on the opposite side of a second modular container. Each arm has a bevel at the end furthest from the container that engages with the edges of the opposing slot to push the arms together as the containers are forced towards each other. When the arms are forced together they can fit through the retaining slot. Once the beveled edges are past the edges of the slot, the arms can return to their initial relative positions, spaced apart, and are thus retained in the slot. Via this mechanism the arms are not removable from the slot and hence the two containers are secured together permanently. This ensures the final constructed system is robust. In a further embodiment there is just one clip arm to engage with the single slot. In a further embodiment, two parallel slots are used, one to engage with each of the two clip arms.

In certain embodiments, the modular storage system includes a support element for supporting a needle container element or two or more connected needle and/or medication container elements, said support element including a flat surface for placing on and being supported by a surface, and wherein the support element is detachably connectable to the said container element or elements by the mutual slidable engagement of a groove or grooves on the support element or container element or elements, and a corresponding projection or projections on the other of the support element or container element or elements.

In certain embodiments, the said support element further includes longitudinal grooves extending along two longitudinal edges of the support element, for slidable engagement with support projections on said container element or elements.

It is common for those with diabetes to lose dexterity, and find it increasingly difficult to handle the delicate devices used in their treatment. It can therefore be advantageous to provide a device that can be attached to a surface so that it no longer needs holding and can be operated using only one hand. A base allows the device to sit on a flat surface where it can be easily used. This base should also be simple to attach and detach to the system. The tongue in groove mechanism, where protruding feet from each container in the system can slide into a long recess provided along the edge of the support element is an example of a simple mechanism.

In order for certain embodiments of the system to be reusable, it can be advantageous to provide a mechanism for opening each container that can be used repeatedly. There are many mechanisms that could be used, such as a lid that screws on or one that snaps on to the rest of each container. However to avoid potential loss of the lid, hinge lids allow each modular container that makes up the medication management system to be opened and sealed again without risk of losing the lid. A hinge lid could be provided that requires a minimum force to open it large enough such that the lid does not open accidently. It could be made to be watertight to protect the pills especially.

BRIEF DESCRIPTION OF THE DRAWINGS

An embodiment of the disclosure will be further described, by way of non-limiting example only, with reference to the accompanying drawings, in which:

FIG. 3a illustrates a first side view of the container of FIG. 1, and FIG. 3b illustrates a second side view of the container of FIG. 1;

FIG. 4a illustrates a perspective view of a needle container from the front.

FIG. 5a illustrates a back view of the container of FIG. 4a, and FIG. 5b illustrates a front view of the container of FIG. 4a;

FIG. 6a illustrates a first side view of the container of FIG. 4a, and FIG. 6b illustrates a second side view of the container of FIG. 4a;

FIGS. 7a and 7b illustrate access doors for use with the first container of FIG. 1 and the needle container of FIG. 4a;

FIG. 8a illustrates a rear view of the container of FIG. 4a, and FIG. 8b illustrates a cut-through view of the container of FIG. 8a;

DETAILED DESCRIPTION

Figure 1:
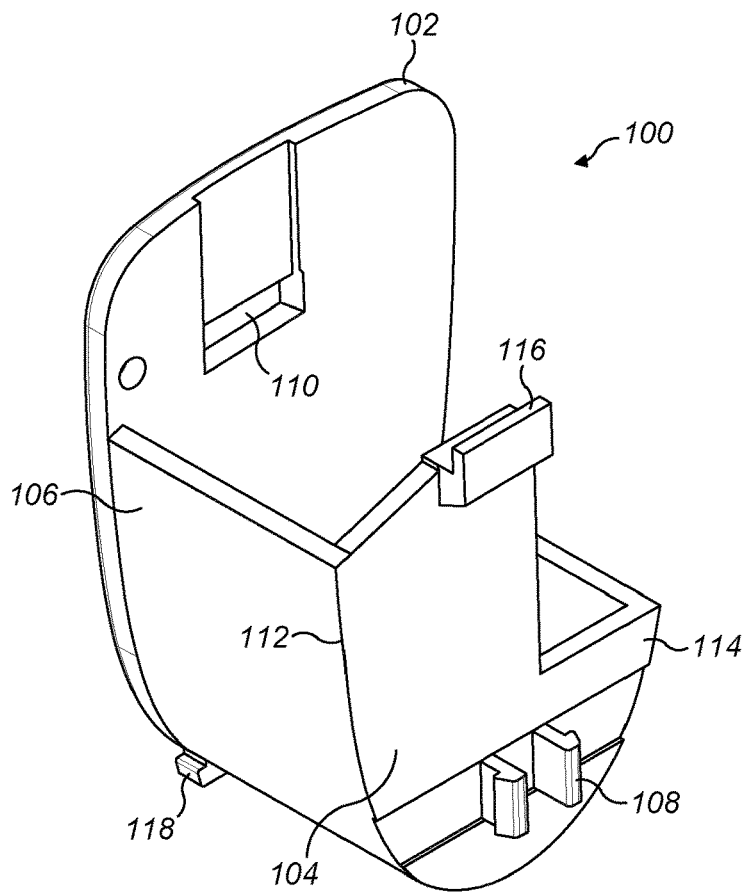
FIG. 1 illustrates a perspective view of a first medical container.

The words top, bottom, up, down, side, end and similar positional language has been used throughout this description according to the relative positions of features when embodiments of the present disclosure are orientated in the position of the embodiments shown in FIG. 1, wherein the front of the container is shown facing left. It is to be understood that the device may be used, stored and transported in any orientation, not just that shown in the figures.

FIG. 1 shows a first medication or pill container 100. This first container, or pill container, is configured to receive pills, tablets, capsules or similar forms of medication. The pill container 100 has a first side wall 102 and a second side wall 104, a base wall 106 and an access door (see FIG. 7a) that together form a compartment for containing the pills. The first side wall 102 has female connector 110 and on the second side wall 104 has male connector 108. In this and the following figures, the apparatus is shown in the orientation that it will most commonly be used in. The side 102, 104 and base walls 106 of the container are formed of rigid plastics such as Acrylonitrile butadiene styrene (ABS).

Figure 2A:
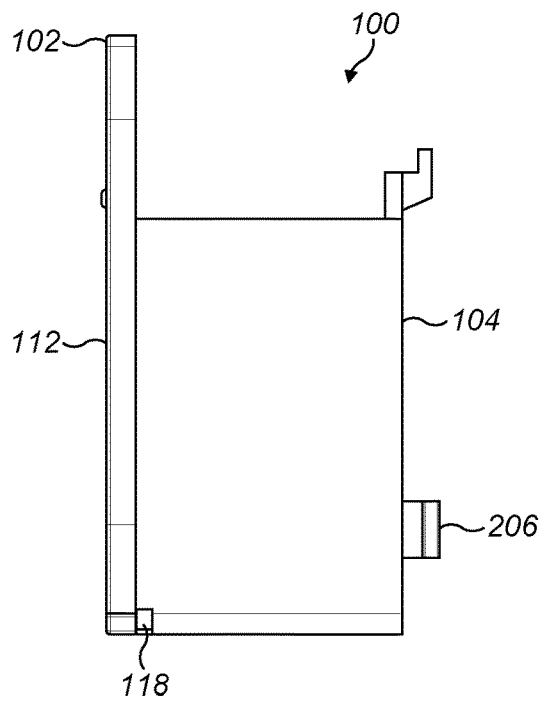
FIG. 2a illustrates a front view of the container of FIG. 1.
Figure 2B:
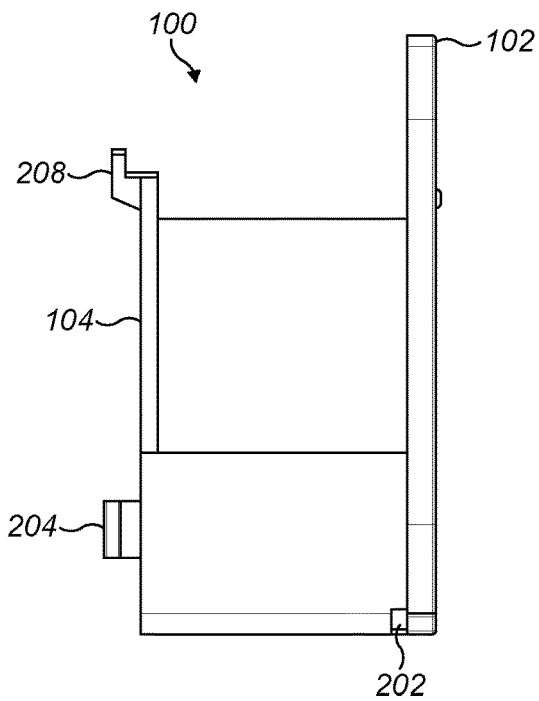
FIG. 2b illustrates a back view of the container of FIG. 1.

FIG. 2a shows a front view of the pill container. The first 102 and second side walls 104 are positioned opposite each other. They both have curved bases. The first side wall 102 is substantially symmetrical about a central vertical axis running from the curved base 105 to the top edge, and it extends the full height of the pill container 100. The second side wall 104 extends part of the way to the full height of the pill container 100 at the front edge 112 and has a lower rear edge 114, shown in FIG. 2b. The top edge 116 of the second wall 104, angles upwards from the point at which it meets the front edge 112, then flattens out to form a flat section before including a step down in height substantially halfway across the width of the wall, to the height of the rear edge 114 of the second wall 104, and extends horizontally to the point at which it meets the rear edge 114. The base wall 106 of the first container 100 is a curved sheet that extends between the two side walls 102, 104. It reaches from the height of the front edge 112 of the second side wall 104 at the front of the container, to the height of the rear edge 114 of the second side wall 104 at the rear of the container. Extending from the edge of the base wall 106 closest for the first side wall 102 of the container is a foot element 118. This foot element 118 is substantially triangular, made of the same material as the base wall 106, and extends such that it has a bottom edge that lies horizontal to the container when it is held in the upright position as in FIGS. 2a and 2b. A second foot 202 extends from the other side of the container 100. These feet 118, 202 are used to stabilize the container 100 in the upright position when placed on a surface.

Two male connectors 108 protrude from the second side wall 104. The first of these male connectors is made up of two parallel arms 204 extending out of the second side wall 104 near the base. At the ends of each arm 204 are tabs 206, extending perpendicular from the arms 204 in a direction away from the neighboring arm. There is a bevel at the end of each tab 206. The second male connector is a hook 208 positioned under the flat section of the top edge 116 of the second side wall 104, parallel with it. The hook 208 extends a short distance outwards from the second side wall 104, then extends upwards, beyond the height of the top edge 116 of the second side wall 104.

The first side wall 102 include two cut outs 302 near the base and a third cut out 304 near the top. These form the female connector of the first container 100. The two cut-outs near the bottom are rectangular slots 302, orientated upwards side-by-side, positioned roughly in the middle of the wall 102, as shown in FIG. 3*a*. The third cut out is a wider rectangular opening 304, orientated at 90° to the bottom two slots 302 and positioned off center. The first wall 102 additionally includes a pivot hole 306, positioned near a top corner of the wall 102 that is configured to receive the axle of the access door (not shown), as well as a pip 308 used to hold the access door open. This pip 308 is a circular projection extending into the compartment from the inner surface of the first side wall 102. The edge of the access door closest to the first side wall 102 can only pass over this pip 308 if a force is applied by the user. The access door can therefore be held open if the door is pushed open to the point at which one edge of the door passes over the pip 308, and the access door is then retained on one side of the pip 308 in the open position.

A second needle container 400 is shown in FIG. 4. The second container 400, or needle container, is configured to receive a needle casing of the type used to hold needles for insulin pens before and after use. Similar to the pill container 100, the needle container 400 has a first side wall 402 and a second side wall 404, a base wall 406 and an access door (not shown) that together form a compartment for containing the needle casing. The needle container 400 additionally has a retaining mechanism within the compartment for retaining the needle casing in position and a hinged clamping element to releasably clamp the needle casing in position.

Referring to FIG. 4, the first side wall 402 of the second container 400 is substantially the same as the first side wall 102 of the medication container 100 described above. The second side wall 404 is also substantially the same. The only difference in the side walls is that as well as the pivot hole 306 in the top corner of the first wall 102 to receive the axle of the access door (see FIG. 7*a*), there are two parallel pivot holes 408 located near the base of both the first 402 and second side walls 404, in the middle of the walls. These holes 408 are configured to receive each end of the axle of the hinged clamping element, discussed further below.

Figure 4B:
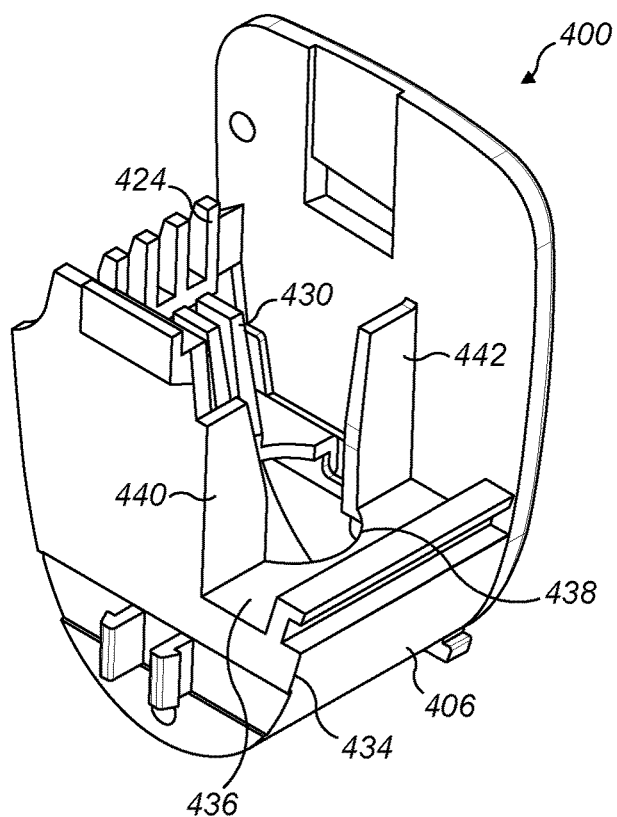
FIG. 4b illustrates a perspective view of the container of FIG. 4a from the rear.

The two side walls 402, 404 are connected along a curved base by a base wall 406 (see FIG. 4*b*). This base wall 406 is a rectangular sheet of plastic curved along the base of the two side walls 402, 404 to connect them. Unlike for the pill container 100 the base wall 406 does not extend up the front edges 410 of the needle container. A first end 412 of the base wall 406 is located at the lowest point of the side walls 402, 404. The front side of the container 400 additionally comprises a front wall 414 connecting the two side walls 402, 404 near the top only. This front wall 414 has a rectangular notch 416 cut in the lower edge 418. Upwards from the inner edge 420 of the front wall 414 extend four vertical protrusions 422. These four protrusions 422 provide flat surfaces 424 inside the container 400 and have curved front edges 426 such that they are narrow at the top and widest at the point where they meet the front wall 414.

Figure 5A:
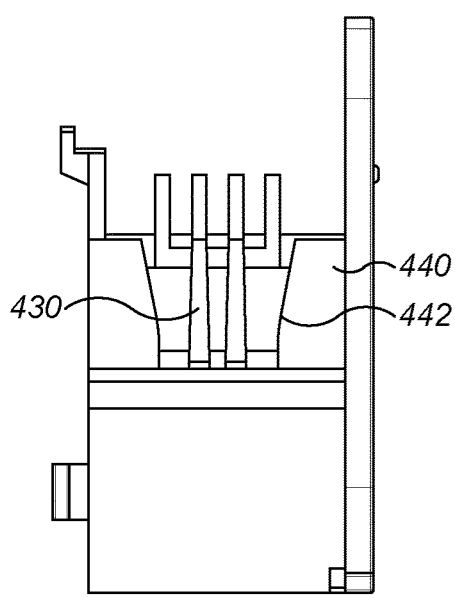

Beneath the front wall 414, and set in from the front edges 410 of the two side walls 402, 404 is a bar 428 that extends between the side walls 402, 404 at the front of the container 400. This bar 428 has a flat top and the two vertical bars 430 extending between the front bar 428 and the front wall 414 extend into the container 400. These vertical bars 430 form part of the internal structure used to aid in the secure storage of a needle casing within the container 400 (see FIG. 5*a*). The flat inner surfaces 432 are angled such that they abut at least part of the substantially conical needle casing 910. Also forming part of the internal structure of the container 400, the sheet of material that forms the base wall 406, at its highest point up the rear wall 434 of the container 400, bends into the container 400 at approximately 90° forming a ledge 436 that extends the full width of the container 400 between the two side walls 402, 404. This ledge 436 extends part way into the container 400, and the end provides a semi-circular cut-out 438. Either side of this cut-out 438, the ledge 436 then extends upwards to form two guides 440 up the side walls 402, 404 of the container 400. These guides 440 are flat sheets of the same material as the base wall 406 that each extends part of the way up the side walls 402, 404 of the container 400 from the ledge 406. They have angled inner edges 442, similar to the inner edges 432 of the vertical bars 430, also to abut at least part of the substantially conical needle casing when inserted. The needle casing, when inserted, slots into the semi-circular cut-out 438 at the end of the ledge 436 of the base wall 406. Together, the ledge 436, the guides 440 and the vertical bars 430 act to guide the conical needle casing into position in the container 400, and hold it in position above the point at which it is clamped.

Figure 5B:
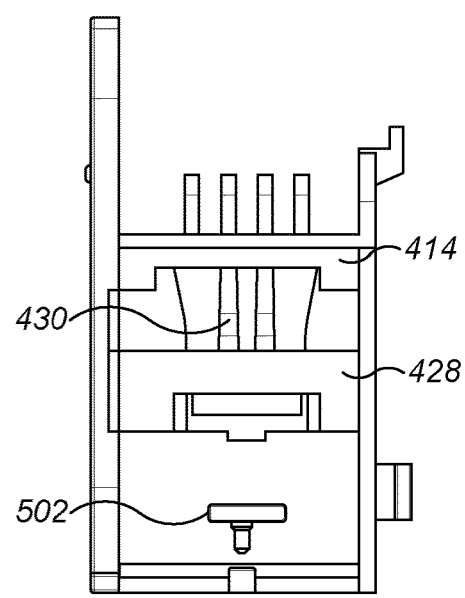

There is a lower shelf 502 present in the container 400, protruding from the base wall 406, as can be seen in FIG. 5*b*. This lower shelf 502 is positioned below the lowest point of the needle casing when it is inserted into the container 400, and extends over halfway across the inside of the compartment, such that a bottom edge of the needle casing can rest on it. At the rear of the ledge 436, where it meets the base wall 406, is a catch 444, protruding upwards from the ledge 436. This catch 444 extends upwards and is bent at approximately 90° at its highest point to create a tab 446, such that it can act as a simple catch, as explained in more detail below.

Figure 6A:
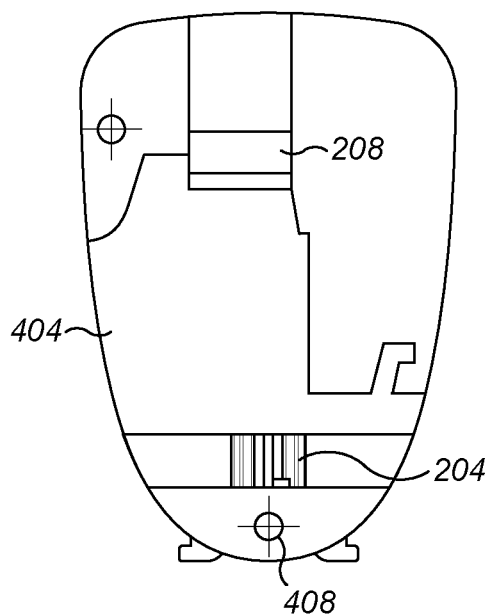
Figure 6B:
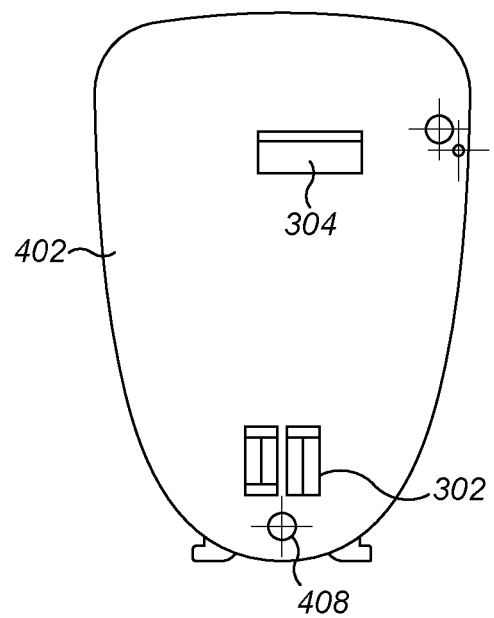

Referring to FIGS. 6*a* and 6*b*, the arrangement of the male 108 and female connectors 110 on the first 402 and second side walls 404 of the second container 400 are the same as the arrangement of the first container 100. The mechanism for attaching the containers is the same. Therefore the pill containers 100 and needle containers 400 described in detail above can be connected in a linear arrangement comprising any combination of needle containers 400 and/or pill containers 100, via the male 108 and female connectors 10. The method is described below for the connection of two pill containers 100.

The hook 208 on the second side wall 104 of a first container 100 aligns with the top rectangular opening 304 of a second container 100'. The hook 208 can be inserted into the opening 304 if the containers are tilted with respect to each other such that the tops are together and the bases are spaced apart. As the bases of the containers are brought together by a user during assembly, the hook 208 of the first container 100 passes into the second container 100', through the opening 304, and upwards. It passes behind the first side wall 102 of the second container 100' and above the top edge of the opening 304, such that it stops the tops of the adjacent containers from separating.

As the bases of the containers are brought together, the two parallel arms 204 on the first container 100 align with the rectangular slots 302 in the first wall 102 of the second container 100'. The arms 204 are configured to align with the slots 302, but the tabs 206 extending from the ends of each arm 204 extend further than the slots 302 are wide. Due to the bevel end of each tab 206, as the arms 204 are pressed into the slots 302, the edges of the slots 302 press against the beveled ends, and the arms 204 are forced towards each other. The arms 204 are forced together until such a point as the ends of the tabs 206 can slide into the rectangular slots 302. Once in the slots 302, there is no longer pressure on the bevel ends and the arms 204 return to their original positions. In these positions the tabs 206 extend past the edges of the slots 302 again, and therefore are retained behind the first side wall 102 of the second container 100'. This mechanism securely attaches the two containers together in a manner that does not then allow them to be taken apart. This mechanism is often referred to as 'snap-fit'.

Figure 7A:
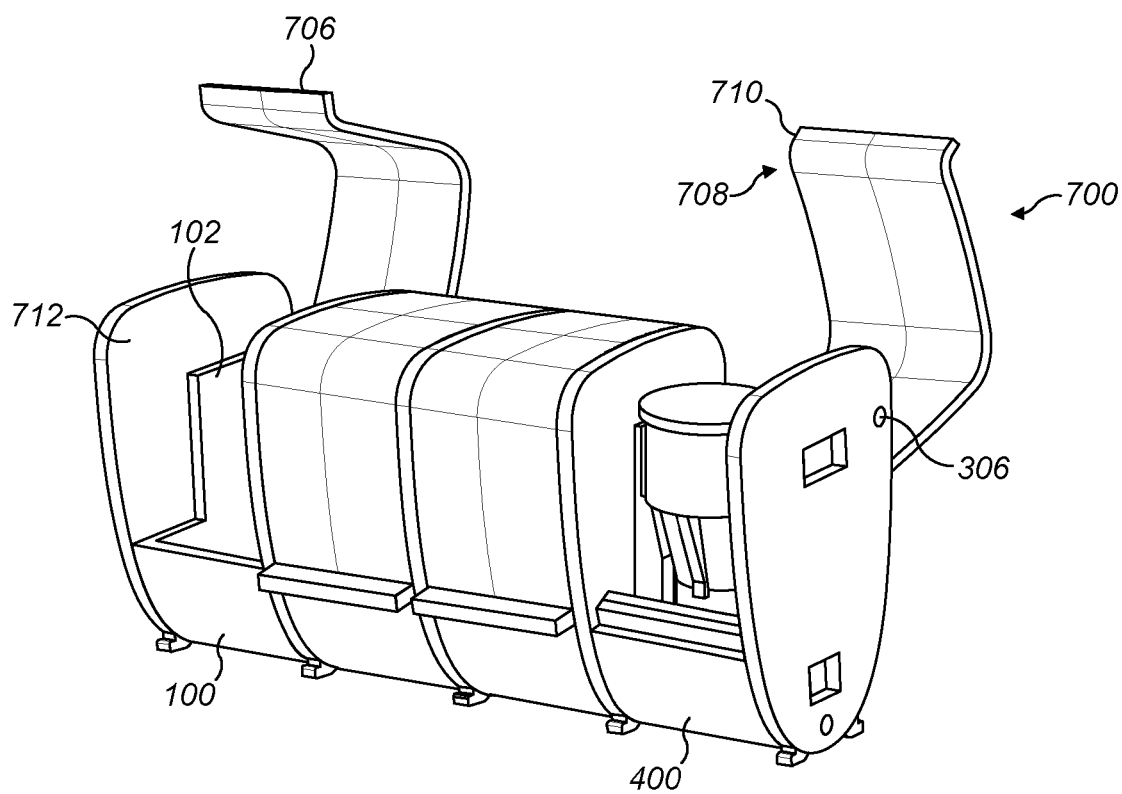
Figure 7B:
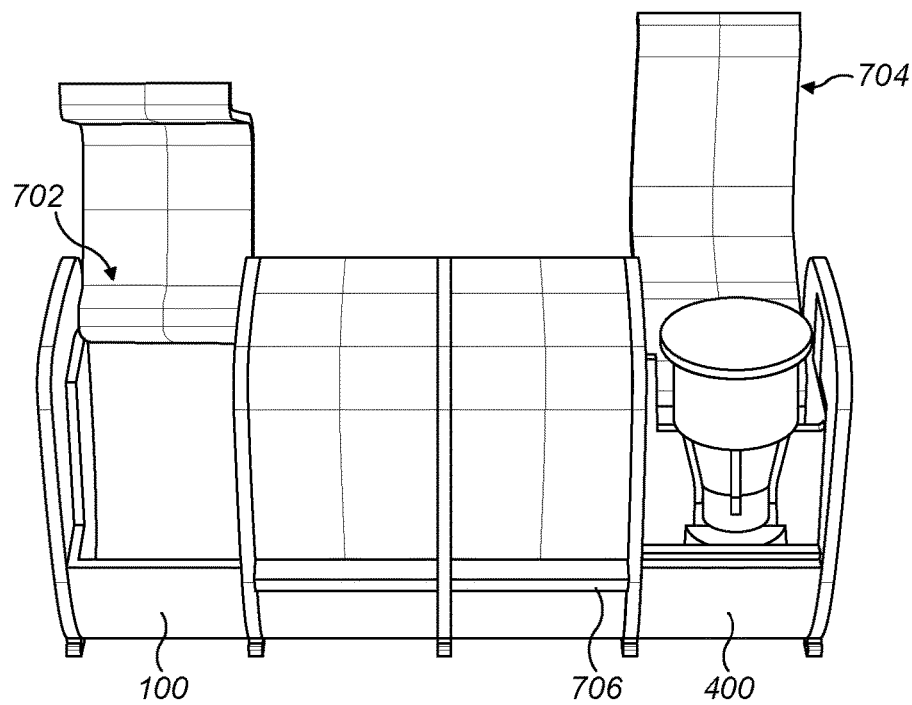

FIGS. 7a and 7b show the access doors 700 of the pill 100 and needle containers 400 that extend between the first and second side walls of each to form an enclosed, sterile compartment. The two doors are substantially identical.

This access door 700 of the container is made from a rigid but transparent material, such as polycarbonate. It is a rectangular sheet of material, curved to follow the contours of the side walls of the container. At one, first end 702 of the access door, the sheet material bends over on itself to create a circular gap (not shown) that extends the full width of the access door 700. This circular gap is configured to receive a pole (not shown) that acts as an axle, extending out of the circular gap 702 at each end. The ends of this axle are received in the pivot hole 306 of the first side wall 102, 402 of each container 100, 400. The axle pole can rotate within the pivot hole 306, allowing the access door 700 to pivot between an open position and a closed position.

At the second end 704 of the hinged door 700, the sheet of the door is bent at substantially 90° to create a handle 706. The inner surface of the door becomes the bottom surface of the handle 706. On this inner surface of the door, positioned above the bend is a rectangular groove 708 that extends across the width of the door 700. The inner surface 710 of the door below the groove 708 engages with the tab 446 of the catch 444 of each container. Due to the flexible nature of the polycarbonate, as the access door 700 is lowered into the closed position, the tab 446 pushes the inner surface 710 outwards, such that it slides over the tab 446 as the door 700 is lowered further, until the point at which the tab 446 is retained within the groove 708. Once the tab 446 is positioned in the groove 708, the lower part of the inner surface 710 cannot pass back over the tab 446. In this way the door is retained in the closed position.

The access door 700 is opened by applying pressure to the bottom surface of the handle 706, bending the door 700 slightly, such that the flat inner surface 710 of the door 700 can pass over the tab 446. In this arrangement the hinged door can be repeatedly opened and sealed.

FIG. 7a additionally shows an end plate 712. This is a sheet of the same material that is used to construct the side walls of the container 400. An end plate 712 has the same height and width as a first side wall 402. An end plate 712 is used at the end of a modular storage system either to seal the openings left by female connectors of the exposed wall of the end container, or to hide the projecting male connectors of the exposed wall of the end container. In the embodiment shown in the figures, and end plate 712 is only shown covering the male connectors extending from the second side wall 104 of the final pill container 100. This end plate will provide slots and an opening (not shown) similar to the female connectors that can be seen on the end needle container 400 in the same figure. These slots and opening are configured to receive the parallel arms 204 and hook 208 of the pill container 100. The same mechanism described above to connect adjacent containers is used to connect the end plate 712 to the end pill container 100. If, as shown in FIG. 7a, the end plate 712 attaches to the second side wall 104 of a pill 100 or needle container 400, it must also provide a pivot hole 306 for the door of the end container.

Figure 8A:
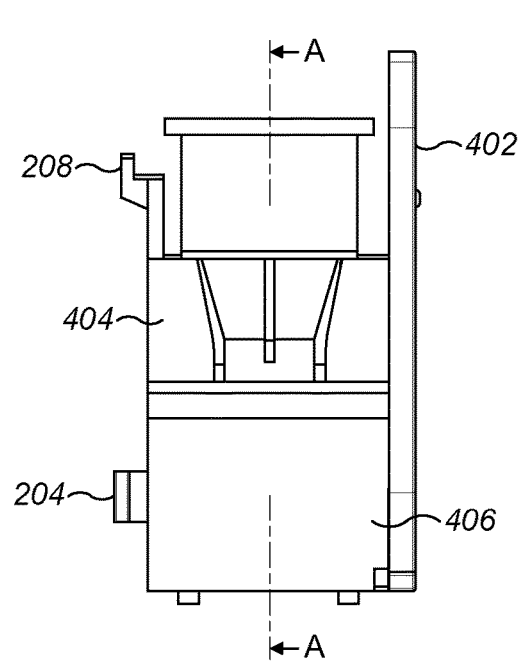
Figure 8B:
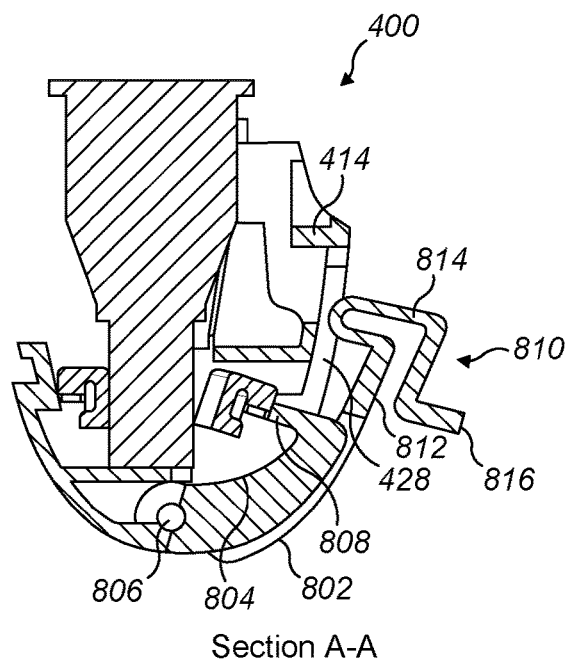
Figure 9A:
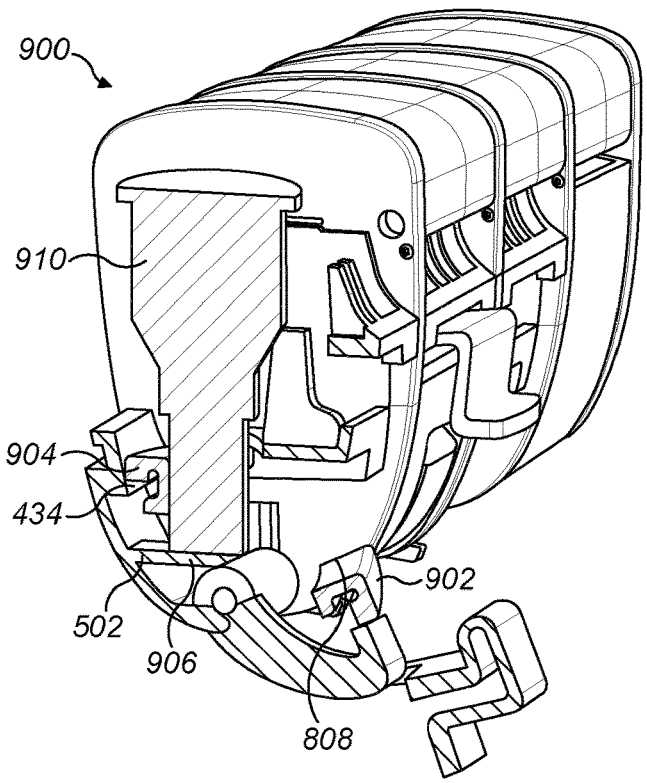
FIG. 9a illustrates a cut-through of the clamping element of the needle container attached to a series of other first or pill containers.
Figure 9B:
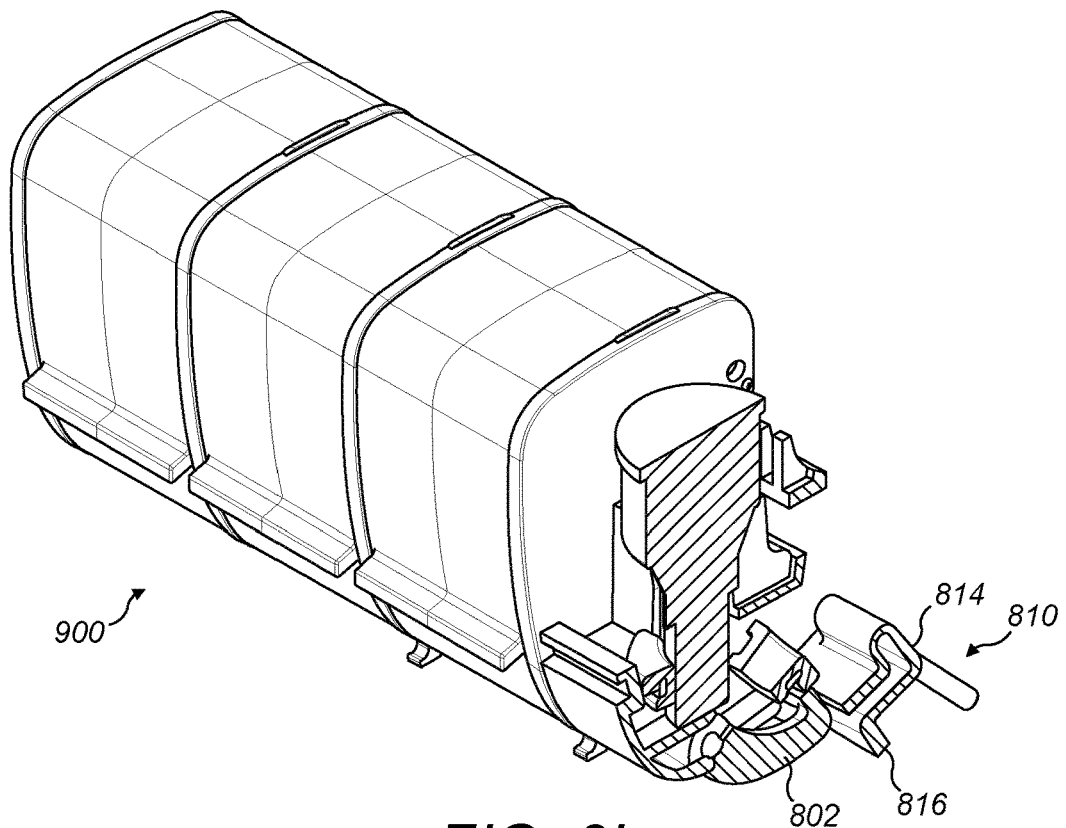
FIG. 9b illustrates the cut-through of FIG. 9b from a rear view.

The second element that completes the sealing of the second, needle container 400 is a hinged clamping element 802. This clamping element 802 is shown in FIG. 8b, as well as in FIGS. 9a and 9b when the needle container 400 is connected to additional containers. The clamping element 802 is positioned at the front of the container 400, towards the base, between the two side walls 402, 404. The clamping element 802 is substantially formed of a rectangular sheet of rigid plastic, made from a material such as Acetyl. At a first end of the clamping element 802, the sheet of material is folded back on itself to the point where it meets the inner surface 804 of the clamping element 802, creating a circular gap 806 that extends across the full width of the clamping element 802. This circular gap 806 is configured to receive a pole (not shown) that acts as an axle, extending out of the circular gap 806 at each end. The axle is retained in the lower pivot holes 408 of the two side walls 402, 404, as described above. The axle pole can rotate within the pivot holes 408, allowing the clamping element 802 to pivot.

At the second end of the clamping element 802, the sheet of material is bent at right angles such that it extends into the container to create a projecting arm 808, as discussed in more detail below. At the corner between the clamping element 802 and the projecting arm 808, a lever 810 extends upwards from the clamping element 802. A first portion 812 of this lever extends upwards to a height slightly above the bar 428 of the container 400 and is then bent at right angles, such that it extends into the container. It is then bent substantially upwards and back on itself and extends in the opposite direction, out from the container. The overlapping section of the sheet forms a compressible tab 814 that is wider than the gap between the bar 428 and the front wall 414 of the container. The end of the lever 810 extends downwards, past the first portion 812 of the lever, then outwards away from the container to create the base of a substantially Z-shaped strip 816. The base portion 816 is thicker than the rest of the sheet material for ease of use. If the base portion 816 of the lever is depressed, the tab 814 is compressed to a width at which it can pass through the gap between the bar 428 and the front wall 414 of the container.

In a closed position the edges of the clamping element 802 engage with the bottom and front edges of the two side walls 402, 404, up to the bottom edge of the front wall. The lever 812 of the clamping element 802 is depressed, compressing the tab 814, such that the tab 814 is narrow enough to slide into a gap underneath the front wall 414 of the container but above the front bar 428. Once the lever 810 is released, the tab 814 expands and is wedged between the front wall 414 and the front bar 428. To open the clamping element 802, the lever 816 is depressed, which compresses the tab 814, allowing it to slide out of the gap between the bar 428 and the front wall 414. In this arrangement the clamping element 802 can be repeatedly opened and sealed.

Extending from the inner surface of the clamping element 802 is a projecting arm 808. The clamping mechanism is comprised of two clamping jaws 902, 904. These are used to retain the needle casing 910 in position in the needle container 400. These clamping jaws 902, 904 are formed from a high friction material such as low surface energy rubber in order to grip the needle casing 910 most effectively. Each clamping jaw 902, 904 has a concave engaging surface 906 configured to receive the curved outer wall of a needle casing 910. In this way the clamping jaws 902, 904 are in contact with the needle casing 910 over a large surface area to increase the grip the jaws have on the casing 910. A first clamping jaw 904 is located on the ledge 434 that extends across the compartment of the container 400 from the base wall 406. At the end of ledge 434 away from the rear of the container the clamping jaw 904 is positioned, such that it can engage with the rear side of a needle casing 910. A second clamping jaw 902 is positioned on the projecting arm 808 of the clamping element 802, at the far end of the arm 808, away from the clamping element 802.

The needle casing 910 is inserted into the container 400 until the base 912 of the casing abuts the lower shelf 502 and cannot move any further. An area of the narrow portion of the casing 910 is in contact with the first clamping jaw 904. The clamping element 802 is then pivoted to a point where it closes. At this point the second clamping jaw 902 on the protruding arm 808 of the clamping element 802 engages with the needle casing 910, opposite the first clamping jaw 904. The needle casing 910 is retained in position between these two clamping jaws 902, 904.

After a needle is removed from the needle casing 910 for use, it can be returned to the needle casing 910 for storage before disposal. In order to dispose of the used needle, held in the needle casing 910, the hinged clamping element 802 is opened such that the second clamping jaw 902 is removed from contact with the needle casing 910. This is done by depressing the lever 816 on the hinged clamping element 802 so that the tab 814 can slide out from within the container 400 and the clamping element 802 is opened. Then, once the access door of the container 400 is opened and the container is tipped upside down, the needle casing 910 will fall from the container 400 via gravity, without exposing the needle.

Once assembled, this storage system 900, comprised of a combination of needle 400 and pill containers 100, may be supported on a surface such as a table, such that it can be used single-handedly. It may further me attached to this surface via some form of clamp or suction mechanism. The support achieved by the addition of a base support 1002. The base support 1002 attaches to the curved bottom of the storage system 900 and provides a flat base that may be positioned on or secured to a surface.

Figure 10A:
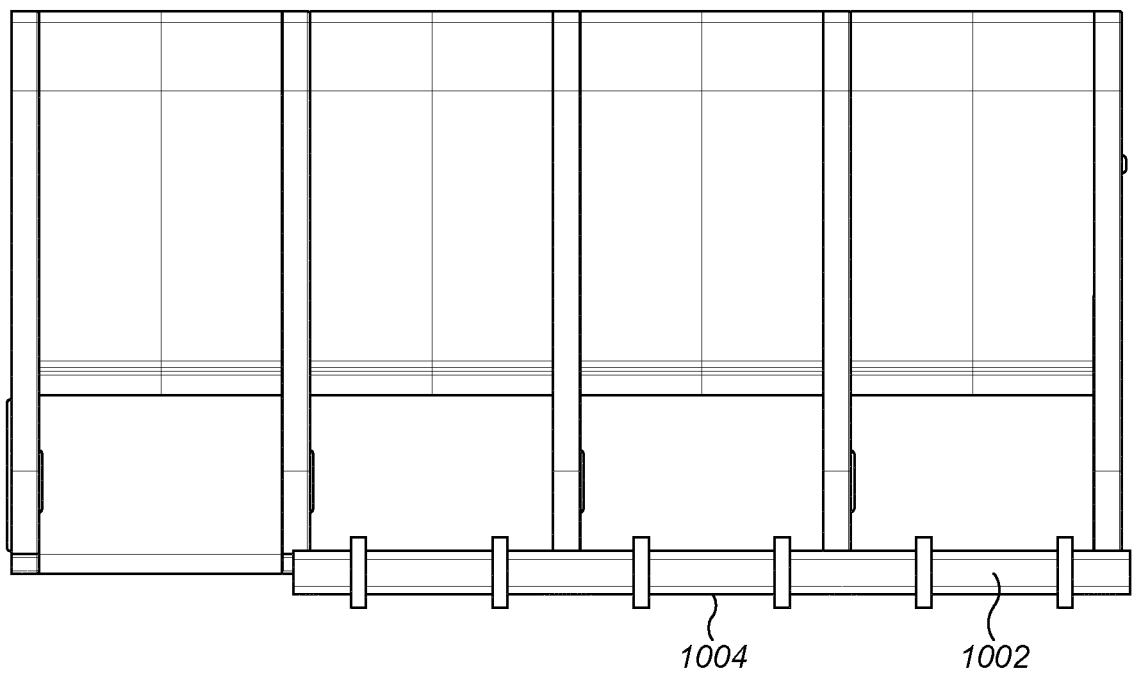
FIG. 10a illustrates a side view of a base support attached to a series of containers.
Figure 10B:
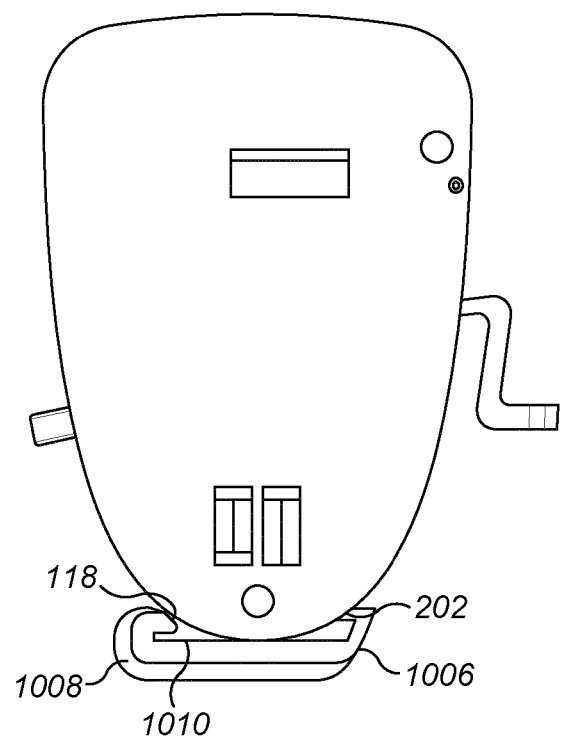
FIG. 10b illustrates a front view of the base support attached to a series of containers.

A base 1002 according to the present disclosure is shown in FIGS. 10a and 10b. The base 1002 is formed of rigid plastics such as ABS. It is a substantially rectangular sheet of material, comprising a bottom face 1004 to engage with the surface and a top surface 1006 to engage with the containers. At each longitudinal edge 1008, the sheet material is bent upwards, away from the bottom surface 1004, and inwards, towards the opposing longitudinal edge 1008 to create elongate recesses 1010 at either edge of the base support 1002. To attach the base support 1002 to the storage system 900, the base support 1002 is slid along the bottom of the storage system 900 from one end such that the feet 118, 202 of the containers slide through the elongate recesses 1010 on either side.

The invention claimed is:

1. A modular storage system for storing a hypodermic needle including:
  a modular needle container element for storing a needle casing for the hypodermic needle, said needle container element including a rigid first wall and a rigid second wall opposing the first wall,
  the needle container element further including a compartment for storing said needle casing, defined by the first and second walls configured to be end walls, and a front wall and a rear wall extending between the first and second walls;
  wherein each of the first and second walls has an outer surface directed away from the compartment, and each of the first and second walls includes either a male connector on the outer surface of the wall or a female connector extending through the wall;
  wherein the male connector includes a clip arm and the female connector includes a slot, such that the male connector is configured for engagement in a snap-fit manner to the female connector in the first or second wall of a second container element; and
  wherein the needle container element includes a needle support structure within the compartment, and a pivotable clamping element, and
  wherein the clamping element includes a first end portion and a second end portion, the first end portion being pivotably connected to a wall of the needle container element and the second end of the clamping element comprising a substantially U-shaped clamp, such that the clamping element is pivotable from a first position in which the needle casing within the needle container element is not in contact with the U-shaped clamp, to a second position in which the U-shaped clamp is engaged with the needle casing.

2. The modular storage system according to claim 1, further including a modular medication container element for storing and/or dispensing medication;
  said medication container element including a rigid first wall and a rigid second wall opposing the first wall, the medication container element further including a compartment for storing said medication, defined by the first and second walls configured to be end walls, and a base wall extending between the first and second walls;
  wherein each of the first and second walls has an outer surface directed away from the compartment, and each of the first and second walls include either a male connector on the outer surface of the wall or a female connector extending through the wall.

3. The modular storage system according to claim 1, wherein the storage system includes further modular needle or medication container elements that are connectable in a linear arrangement with the modular container element, such that the male connector of one engages with the female connector of the other.

4. The modular storage system according to claim 1, wherein the first or second wall includes a hook on the outer surface of the wall and the first or second wall includes an opening extending through the wall to receive the hook, such that the hook is configured for engagement with a corresponding opening in the first or second wall of a second container element.

5. The modular storage system according to claim 4, wherein the hook is positioned on the outer face of the first or second wall that includes the clip arm and the opening is positioned through the first or second wall that includes the slot.

6. The modular storage system according to claim 1, wherein the storage system includes an end plate element, said end plate element comprising a rigid wall, couplable to the first or second wall of said container element.

7. The modular storage system according to claim 6, wherein the end plate element has two opposing surfaces, a first smooth surface and a second surface including either a male connector on the second surface or a female connector extending through the end plate element.

8. The modular storage system according to claim 7, wherein the male connector includes a clip arm and the female connector includes a slot, such that the male connector is configured for engagement in a snap-fit manner to the female connector in the first or second wall of a container element.

9. The modular storage system according to claim 1, wherein the male connector includes two clip arms and the female connector includes the slot, such that the arms are configured to engage in a snap-fit manner with the slot of a second container.

10. The modular storage system according to claim 1, wherein the modular storage system includes a support element for supporting the needle container element or two or more connected needle and/or medication container elements, said support element including a flat surface for placing on and being supported by a surface, and wherein the support element is detachably connectable to the said container element or elements by mutual slidable engagement of a groove or grooves on the support element or container element or elements, and a corresponding projection or projections on the other of the support element or container element or elements.

11. The modular storage system according to claim 10, wherein the support element further includes longitudinal grooves extending along two longitudinal edges of the support element, for slidable engagement with support projections on said container element or elements.

* * * * *

UNITED STATES PATENT AND TRADEMARK OFFICE
CERTIFICATE OF CORRECTION

| | |
|---|---|
| PATENT NO. | : 11,266,477 B2 |
| APPLICATION NO. | : 16/976068 |
| DATED | : March 8, 2022 |
| INVENTOR(S) | : Clive Peter Gunther |

It is certified that error appears in the above-identified patent and that said Letters Patent is hereby corrected as shown below:

On the Title Page

Item (71), Applicant
Delete "NEEDLERAY"
Insert -- NEEDLEBAY --

Signed and Sealed this
Fifteenth Day of November, 2022

*Katherine Kelly Vidal*

Katherine Kelly Vidal
*Director of the United States Patent and Trademark Office*